(12) United States Patent
Kaethner et al.

(10) Patent No.: US 12,159,705 B2
(45) Date of Patent: Dec. 3, 2024

(54) METHOD FOR DETERMINING AN IMAGING PARAMETER VALUE FOR THE CONTROL OF A MEDICAL TECHNOLOGY DEVICE DURING A CAPTURE OF A FIRST IMAGE DATASET

(71) Applicant: Siemens Healthcare GmbH, Erlangen (DE)

(72) Inventors: Christian Kaethner, Forchheim (DE); Alois Regensburger, Poxdorf (DE); Gregor Niewalda, Buckenhof (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 258 days.

(21) Appl. No.: 17/687,743

(22) Filed: Mar. 7, 2022

(65) Prior Publication Data

US 2022/0293250 A1 Sep. 15, 2022

(30) Foreign Application Priority Data

Mar. 9, 2021 (DE) ...................... 10 2021 202 293.6

(51) Int. Cl.
*G16H 30/40* (2018.01)
*G06T 7/246* (2017.01)
*G16H 40/67* (2018.01)

(52) U.S. Cl.
CPC ............. *G16H 30/40* (2018.01); *G06T 7/246* (2017.01); *G16H 40/67* (2018.01); *G06T 2207/30004* (2013.01)

(58) Field of Classification Search
CPC ........ G16H 30/40; G16H 40/67; G16H 20/40; G16H 30/20; G16H 40/63; G06T 7/246; G06T 2207/30004; G06T 7/0012; G06T 7/13; G06T 7/20; G06T 2207/20081; G06N 20/00
USPC ........................................................ 382/128
See application file for complete search history.

(56) References Cited

U.S. PATENT DOCUMENTS

| 9,545,238 | B2* | 1/2017 | Bertsch ................ A61B 6/5217 |
| 9,760,830 | B2* | 9/2017 | Becker .................. G06T 11/005 |
| 2009/0005669 | A1 | 1/2009 | Schmidt et al. |
| 2009/0012821 | A1 | 1/2009 | Besson et al. |

(Continued)

FOREIGN PATENT DOCUMENTS

| CN | 101332086 A | 12/2008 |
| EP | 3437561 A1 | 2/2019 |

*Primary Examiner* — Juan A Torres
(74) *Attorney, Agent, or Firm* — Harness, Dickey & Pierce, P.L.C.

(57) ABSTRACT

At least one example embodiment relates to a computer-implemented method for determining an imaging parameter value for the control of a medical technology device during a capture of a first image dataset. In this context, the first image dataset is provided to be transferred from the medical technology device to a remotely arranged device. The method comprises at least one of receiving or determining a transfer parameter value. In this context, the transfer parameter value comprises an information item concerning which image information is relevant for the first image dataset which is to be transferred. The method further comprises determining the imaging parameter value based on the transfer parameter value. The method further comprises providing the imaging parameter value.

20 Claims, 3 Drawing Sheets

(56) References Cited

U.S. PATENT DOCUMENTS

| | | | |
|---|---|---|---|
| 2010/0037394 A1* | 2/2010 | Hayes | A61B 5/055 |
| | | | 5/601 |
| 2016/0217569 A1 | 7/2016 | Bhatia et al. | |
| 2017/0053414 A1* | 2/2017 | Flohr | A61B 6/12 |
| 2017/0086798 A1 | 3/2017 | Bjaerum et al. | |
| 2018/0360398 A1 | 12/2018 | Wenderow et al. | |
| 2019/0038251 A1 | 2/2019 | Pickert | |
| 2019/0295294 A1* | 9/2019 | Fournie | G06T 11/006 |
| 2020/0107796 A1 | 4/2020 | Regensburger | |

* cited by examiner

METHOD FOR DETERMINING AN IMAGING PARAMETER VALUE FOR THE CONTROL OF A MEDICAL TECHNOLOGY DEVICE DURING A CAPTURE OF A FIRST IMAGE DATASET

CROSS-REFERENCE TO RELATED APPLICATION(S)

The present application hereby claims priority under 35 U.S.C. § 119 to German patent application number DE 102021202293.6 filed Mar. 9, 2021, the entire contents of which are hereby incorporated herein by reference.

FIELD

At least some example embodiments relate to computer-implemented methods for determining an imaging parameter value for the control of a medical technology device during a capture of a first image dataset. Example embodiments also relate to determining systems, computer program products and computer-readable storage mediums.

BACKGROUND

It is known to monitor and/or control a medical intervention on an examination object, for example, by medical imaging. For this purpose, an image dataset of the examination object is typically captured with a medical technology device. Typically, the image dataset comprises at least one medical image. The image dataset often comprises a temporal sequence of individual medical images of the examination object. In other words, the image dataset can comprise a video sequence. When capturing the image dataset, the medical technology device can be controlled, in particular, by an imaging parameter. It is known to transfer the image dataset to a remotely arranged device. For example, in this way a medical practitioner or treating person or operator can be located in another room or in another building or in another city or in another country from the examination object to monitor and/or carry out the medical intervention. The medical practitioner can monitor and/or carry out the medical intervention at the remotely arranged device.

For this purpose, it is necessary that the image dataset is transferred without delay or with as little time delay as possible to the remotely arranged device. The transfer is in this context limited, in particular, by a data transfer rate. Typically, the image dataset is compressed such that the transfer is possible with a minimum of time delay. Alternatively, a time delay is taken into account. During the compression of the image dataset, image information items included by the image dataset are typically lost. In other words, typically, more image information items are captured than are made available to the medical practitioner at the remotely arranged device. The examination object can be exposed to X-ray radiation during the capture of the image dataset. Herein, a radiation dose, or dose, is applied to the examination object. This dose is to be kept as small as possible. More image information items in the image dataset are often associated with a higher dose for the examination object. In addition, more image information items are often associated with a greater time and/or cost expenditure during capture and/or transfer of the image dataset. For this reason, the image dataset should comprise only the scope of image information items or only the image information items which can also be transferred to the remotely arranged device. The image information items actually transferred can also be designated relevant image information items.

In addition, an image dataset is often captured, during positioning of the medical technology device, for monitoring the positioning. During positioning, the medical technology device is moved relative to the examination object. It is in this context necessary to provide to the medical practitioner an overview of the current positioning of the medical technology device relative to the examination object. It is known to maintain an imaging parameter value that is suitable for the medical intervention during the positioning of the medical technology device.

SUMMARY

It is possible to reduce a quality of the image dataset during positioning of the medical technology device as compared with a quality of the image data set during monitoring and/or carrying out the medical intervention. In other words, the image dataset can comprise fewer image information items during positioning than during monitoring and/or carrying out the medical intervention. In other words, it is often not necessary for the image dataset to comprise exactly as many image information items during positioning as the image dataset during monitoring and/or carrying out the medical intervention. In particular, the image dataset comprises fewer relevant image information items during positioning than during monitoring and/or performance of the medical intervention. Thus, during positioning, a dose applied to the examination object could be reduced if X-ray radiation is used for capturing the image dataset. Alternatively or additionally, time and/or cost could be reduced during capture of the image dataset for the positioning.

At least one example embodiment provides a computer-implemented method for determining an imaging parameter value for the control of a medical technology device during a capture of a first image dataset, wherein the first image dataset is to be transferred from the medical technology device to a remotely arranged device, the method including at least one of receiving or determining a transfer parameter value, wherein the transfer parameter value includes an information item concerning which image information is relevant for the first image dataset which is to be transferred; determining the imaging parameter value based one the transfer parameter value; and providing the imaging parameter value.

At least one example embodiment provides a determining system for determining an imaging parameter value for the control of a medical technology device during a capture of a first image dataset, wherein the first image dataset is to be transferred from the medical technology device to a remotely arranged device, the determining system comprising: an interface; and a computing device, wherein at least one of the interface or the computing device is configured to at least one of receive or determining a transfer parameter, the transfer parameter value comprises an information item concerning which image information is relevant for the first image dataset which is to be transferred, the computing unit is also configured to determine the imaging parameter value based on the transfer parameter value, and the interface is also configured to provide the imaging parameter value.

At least one example embodiment provides a computer program product having a computer program which is directly loadable into a memory store of a determining system, having program portions when executed by the determining system to cause the determining system to perform a method according to example embodiments.

At least one example embodiment provides a computer-readable storage medium on having instructions, when executed by a determining system, configured to cause the determining system to perform a method according to example embodiments.

BRIEF DESCRIPTION OF THE DRAWINGS

The above described properties, features and advantages of example embodiment are more clearly and distinctly described in the context of the following description making reference to the drawings. The drawings and descriptions do not restrict example embodiments in any way. In different figures, the same components are provided with corresponding reference signs. The drawings are in general not to scale.

In the drawings.

DETAILED DESCRIPTION

Figure 1:
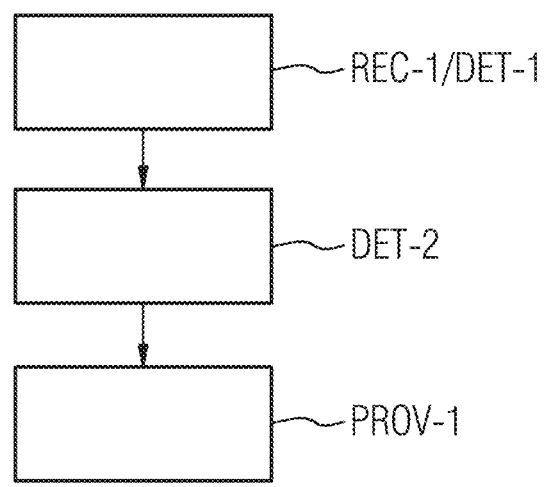
FIG. 1 shows a first exemplary embodiment of a method for determining an imaging parameter value for the control of a medical technology device during a capture of a first image dataset.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one example embodiment, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least some example embodiments provide a method which enables an adaptation of the imaging parameter value such that only the image information items that are relevant to a medical practitioner are captured.

This may be achieved by a method for determining an imaging parameter value for the control of a medical technology device during a capture of a first image dataset by a device for determining an imaging parameter value for the control of a medical technology device during a capture of a first image dataset by a computer program product and by a computer-readable storage medium according to the independent claims. Advantageous developments are disclosed in the dependent claims and in the following description.

At least some example embodiments are described below, both in relation to the claimed devices and also in relation to the claimed method. Features, advantages or alternative embodiments mentioned herein are also transferable similarly to the other claimed subject matter and vice versa. In other words, the object-related claims (which are directed, for example, to a device) can also be further developed with the features described or claimed in relation to a method. The corresponding functional features of the method are thereby provided by corresponding physical modules.

At least one example embodiment relates to a computer-implemented method for determining an imaging parameter value for the control of a medical technology device during a capture of a first image dataset. In this context, the first image dataset is provided to be transferred from the medical technology device to a remotely arranged device. In this context, the method comprises a method step of capturing and/or determining a transfer parameter value. In this context, the transfer parameter value comprises an information item concerning which image information or which scope of image information is relevant for the first image dataset which is to be transferred. The method further comprises a method step of providing the imaging parameter value dependent upon the transfer parameter value. The method further comprises a method step of providing the imaging parameter value.

The medical technology device can be, in particular, an imaging medical technology device. In other words, the medical technology device can be configured for capturing medical images and/or image datasets. The medical technology device can be, in particular, an angiography system, a C-arm system, a computed tomography system, a magnetic resonance tomography system, an ultrasound system and/or an optical coherence tomography system, etc.

The medical technology device can be controllable, in particular, by the imaging parameter value. In other words, the medical technology device can be controlled by way of the imaging parameter value during capture of the first image dataset. In this context, the imaging parameter value can specify a value for capturing the first image dataset. For example, the imaging parameter value can specify a voltage of an X-ray tube, a current of the X-ray tube, an exposure time and/or an acquisition time, an image acquisition frequency and/or a binning of a detector, etc. during the capture of the first image dataset. In particular, by way of the imaging parameter value, an image information item included by the first image dataset can be controlled. In other words, the image information included by the first image dataset can depend upon the imaging parameter value.

The first image dataset in this context includes at least one medical image. In this context, the medical image comprises a recording with the medical technology device. The medical image can comprise, for example, an X-ray image, a slice image and/or a three-dimensional image and/or a subtraction image and/or a summation image, etc. The medical image can be, in particular, a pixelated image. The pixelated image comprises a plurality of pixels which are arranged in a pixel matrix. An image value is in this context associated with each pixel. Alternatively, the medical image can be a voxelated image. The voxelated image comprises a plurality of voxels which are arranged in a voxel matrix. An image value is associated with each voxel. In particular, the first image dataset can comprise a temporal sequence of medical images. In other words, the first image dataset can comprise a video sequence of medical images. In particular, the temporal spacing between the individual medical images can be specified by way of the image acquisition frequency.

The first image dataset can be configured, in particular, to be transferred to the remotely arranged device. By the transfer, the first image dataset is also available on the remotely arranged device. In particular, the first image dataset can be configured to be displayed on the remotely arranged device.

Besides a data transfer connection, the remotely arranged device can be, in particular, separate from the medical technology device. In other words, the remotely arranged device is independent of the medical technology device. In particular, the remotely arranged device can be spatially separate from the medical technology device. In particular, the remotely arranged device can in this context be arranged in the same room as the medical technology device. Alternatively, the remotely arranged device can be arranged in a different room and/or in a different building and/or in a different city and/or in a different country from the medical technology device. In particular, the remotely arranged device is configured for a data transfer with the medical technology device. In particular, the first image dataset can be transferred by way of a data transfer from the medical technology device to a remotely arranged device. In particular, the first image dataset can be transferred via a local area network (LAN) or a wireless local area network (WLAN) and/or via a mobile communications network. In particular, the remotely arranged device can be configured to display the first image dataset and/or the at least one medical image included by the first image dataset, by a display unit. In this context, the display unit can comprise a screen and/or monitor. The monitor can be a field emission display (FED), a liquid crystal display (LCD), a thin film transistor screen (TFT-LCD), a cathode ray tube screen (CRT), a plasma screen, an organic light emitting diode display (OLED) and/or a surface conduction electron emitter display (SED). In particular, the first image dataset can be displayed to a medical practitioner. In this context, the medical practitioner can carry out and/or observe and/or monitor a medical intervention on the basis of the first image dataset.

In the method step of receiving and/or determining a transfer parameter value, the transfer parameter value can be received, in particular, by an interface and/or can be determined by a computing unit. In this context, the transfer parameter value comprises an information item concerning which image information is relevant for the first image dataset which is to be transferred. In particular, the transfer parameter value can describe which image information of the first image dataset can actually be transferred. In other words, the transfer parameter value can comprise a restriction or limitation on the transfer of the first image dataset. In particular, the actually transferrable image information can correspond to the relevant image information or can limit the relevant image information. Alternatively or additionally, the transfer parameter value can describe which image information is actually needed, for example, dependent upon a progress of the medical intervention. In other words, the transfer parameter value can describe which image information is actually relevant for the medical practitioner when performing and/or monitoring the medical intervention, dependent upon the progress or the relevant method step of the medical intervention. For example, for a positioning of the medical technology device, a first image dataset with fewer image information items is needed than when performing an image-controlled surgical or interventional treatment. The first image dataset for positioning the medical technology device thus comprises fewer relevant image information items than the first image dataset which is used for the performance of the surgical intervention by the medical practitioner. The transfer parameter can comprise, for example, an information item concerning the purpose for which, and/or in which regard, the first image dataset is needed and/or used.

In the method step of receiving the transfer parameter value, the transfer parameter value can be received from a database and/or a manual input. In particular, a plurality of transfer parameter values can be stored in the database for different purposes and/or situations. Alternatively or additionally, the medical practitioner or another member of medical staff can provide the transfer parameter value manually. In particular, the transfer parameter value can be provided manually by an input unit.

In the method step of determining the transfer parameter value, the transfer parameter value can be determined on the basis of a current situation and/or a current technical condition.

In the method step of determining the imaging parameter value, the imaging parameter value is determined dependent upon the transfer parameter value. In particular, the imaging parameter value is determined by the computing unit. In particular, the imaging parameter value is determined in such a way that the first image dataset captured on the basis of the imaging parameter value comprises the relevant image information. In particular, the imaging parameter value is determined in such a way that the first image dataset captured on the basis of the imaging parameter value comprises no more than the relevant image information. In particular, the imaging parameter value can be determined in such a way that it is not necessary to compress the first image dataset before the transfer in a lossy manner. A lossy compression can be, for example, a binning of a medical image included by the first image dataset. In particular, image information items lost through the binning can no longer be subsequently reconstructed. In particular, the imaging parameter value can be determined in such a way that none of the image information of no interest to the medical practitioner and/or none of the medical images or image portions of no interest to the medical practitioner are included by the first image dataset.

In the method step of providing the imaging parameter value, the imaging parameter value is provided, in particular, by the interface. In particular, the imaging parameter value for the control of the medical technology device is provided. In other words, the imaging parameter value is provided to the medical technology device. In particular, the first image dataset can be captured on the basis of the imaging parameter value. In other words, the medical technology device can be controlled by the imaging parameter value during capture of the first image dataset.

In particular, the method steps of receiving and/or determining the transfer parameter value, determining the imaging parameter value and/or providing the imaging parameter value can be carried out by an interface and/or a computing unit of the medical technology device. Alternatively or additionally, the method steps of receiving and/or determining the transfer parameter value, determining the imaging parameter value and/or providing the imaging parameter value can be carried out by an interface and/or a computing unit of the remotely arranged device.

The inventors have discovered that an applied dose, time and/or costs can be reduced by a flexible adaptation of the imaging parameter value. In particular, the inventors have discovered that for this purpose, the imaging parameter value can be adapted dependent upon the transferrable image information and/or the image information of interest to a medical practitioner. In other words, the imaging parameter value can be adapted dependent upon the relevant image information. In particular, for this purpose, in advance of the capture of the first image dataset, the transfer parameter value can be determined dependent upon the current situation. In this context, the transfer parameter value comprises a limit for the relevant image information. In other words, the transfer parameter value comprises a value which limits the image information of the first image dataset to the relevant image information. The inventors have discovered that the imaging parameter value can be determined on the basis of the transfer parameter value.

According to at least one example embodiment, the imaging parameter value is determined in such a way that a quality of the first image dataset is limited by the relevant image information.

The quality of the first image dataset is quantified, for example, by a spatial and/or temporal resolution and/or by a signal-to-noise ratio. The image information of the first image dataset is dependent, in particular, upon the quality of the first image dataset. For example, the spatial resolution determines the smallest structure which can be represented in the first image dataset. In other words, the spatial resolution determines the smallest structure about which information items are included by the image information.

Thus, the imaging parameter value is determined in such a way that the image dataset comprises not more than the relevant image information. In particular, the imaging parameter value specifies the quality of the first image dataset. In particular, the imaging parameter value can comprise the image acquisition frequency and/or the binning and/or the exposure time and/or the dose and/or the recording dose. For example, the image acquisition frequency can specify the temporal resolution. Alternatively or additionally, the binning or the exposure time or the dose can specify the spatial resolution. For example, the imaging parameter value is determined in such a way that the spatial and/or temporal resolution is not greater than can be transferred. In other words, the first image dataset should not comprise more medical images or a medical image should not comprise more pixels and/or voxels than can be transferred in a medically useful way. Medically useful means that a time delay due to the transfer should be minimized. In particular, the first image dataset should be transferred in real time. In particular, a maximum time delay of 500 ms is tolerable and medically useful. If the first image dataset comprises a sequence of medical images, the time that the transfer of a medical image requires should not be greater than the temporal spacing between the capture of two mutually sequential medical images of the sequence. Alternatively or additionally, the imaging parameter value is determined in such a way that the first image dataset comprises no more image information items than are of interest or relevance to the medical practitioner. In particular, the quality of the first image dataset should not be better than is required by the medical practitioner. The quality needed in this context corresponds to the necessary and/or relevant image information. In particular, therefore, the relevant image information serves as a limit for the quality of the first image dataset, which is itself specified by the imaging parameter.

The inventors have discovered that the quality of the first image dataset can be delimited by the relevant image information items. Additional image information items which are obtained by way of a better quality are not relevant and lead to an unnecessary radiation load and/or costs and/or time loss. The inventors have discovered that the quality of the first image dataset is specified by the imaging parameter value.

According to at least one example embodiment, the transfer parameter value comprises a first data transfer rate.

In particular, the first data transfer rate describes a data quantity or a data volume that can be transferred in a particular time interval. The expression data rate is often used as a synonym for the expression data transfer rate. The data transfer rate is typically given in bits per second (bit/s).

The first data transfer rate states, in particular, how high the data transfer rate is at a time point at which the first image dataset is to be transferred. In particular, the first data transfer rate specifies a mean data transfer rate for a time interval in which the first image dataset is to be transferred. The first data transfer rate therefore states a limit of an image information item that can actually be transferred in a time interval. In this context, the image information that can actually be transferred limits the relevant image information. Image information that cannot be transferred is not relevant.

If the first image dataset is transferred via a 5G mobile communication network, the first data transfer rate can correspond to the reserved data transfer rate.

In particular, the imaging parameter value can be determined on the basis of the first transfer rate. In particular, the imaging parameter value can then be determined such that the first image dataset comprises a data quantity that can be transferred within a predetermined timespan of, for example, 500 ms. If the first image dataset comprises a temporal sequence of medical images, the image acquisition frequency included by the imaging parameter value can be selected such that the duration during transfer of a medical image of the sequence corresponds to not more than the temporal spacing during capture of the medical images. In other words, the image acquisition frequency can be selected such that a "backlog" during the transfer of the medical images of the temporal sequence due to the data transfer rate can be prevented.

The inventors have discovered that the relevant image information is limited by the image information that can actually be transferred in a particular time interval. The inventors have discovered that the image information that can actually be transferred is also limited by the first data transfer rate. The inventors have discovered that, on the basis of the first data transfer rate, the imaging parameter value can be determined in such a way that the first image dataset comprises a data quantity that can be transferred within a predetermined time interval. The inventors have discovered that in this way, it can be prevented that the first image dataset must be compressed in a lossy manner and that image information items are partially not transferred. Such non-transferred image information items have been captured unnecessarily and lead to an unnecessarily applied dose and/or radiation load, time loss and/or costs.

According to at least one example embodiment, the method step of determining the transfer parameter value also comprises a method step of determining the first data transfer rate for a time point of the transfer of the first image dataset.

In particular, the time point of the transfer of the first image dataset is the time point at which the first image dataset is to be transferred to the remotely arranged device. In particular, the time point of the transfer of the first image dataset can also correspond to a timespan. In particular, the first image dataset can then be transferred over a timespan if the first image dataset comprises a temporal sequence of medical images. For example, the timespan can correspond to the duration of the sequence.

In particular, the first data transfer rate for the time point of the transfer of the first image dataset can be retrieved in the method step of determining the first data transfer rate. In particular, the first data transfer rate can be retrieved if the data transfer rate is not temporally variable. In particular, the first data transfer rate can be retrieved if the data transfer rate for the time point of the transfer of the first image dataset is known, in particular, is reserved. In particular, the data transfer rate can be known for a transfer via a 5G mobile communications network and for the time point of the transfer.

Alternatively or additionally, the first data transfer rate can be estimated on the basis of experiential values in the method step of determining of the first data transfer rate. An experiential value can be, for example, knowledge of a typical data transfer rate at a particular time and/or on a particular day of the week.

Alternatively or additionally, the first data transfer rate can be determined on the basis of a data transfer rate determined before the time point of the transfer of the first image dataset. The data transfer rate before the time point of the transfer of the first image dataset can thereby be measured. The first data transfer rate can be derived from this data transfer rate. For example, the first data transfer rate can correspond to the data transfer rate before the time point of the transfer of the first image dataset. Alternatively, a fixed fraction of the data transfer rate before the time point of the transfer of the first image dataset can be assumed for the first data transfer rate. In particular, it can be assumed that the first data transfer rate is not smaller than this fraction. The fraction can comprise, for example, 90% or 80% or 70%.

The inventors have discovered that the first data transfer rate at the time point of the transfer of the first image dataset is limiting for the transfer of the first image dataset. In particular, the imaging parameter can be determined exactly for the first data transfer rate that is available at the time point of the transfer of the image dataset, regardless of temporal variations before or after the transfer. In other words, temporal variations of the data transfer rate can be ignored if the first data transfer rate at the time point of the transfer of the first image dataset is known.

According to at least one example embodiment, in the method step of determining the first data transfer rate, the first data transfer rate is predicted on the basis of a plurality of second data transfer rates. In this context, the plurality of second data transfer rates is determined before the time point of the transfer of the first image dataset.

On the basis of the plurality of second data transfer rates, a variance of the data transfer rate over time can be determined. In particular, the first data transfer rate can then correspond to a mean value or a median of the plurality of the second data transfer rates.

In particular, the plurality of second data transfer rates can be determined and/or captured erratically and/or at random time points before the time point of the transfer of the first image dataset.

Alternatively, the plurality of second data transfer rates can comprise a temporal sequence of second transfer rates. In particular, two second data transfer rates of the plurality of second data transfer rates can be captured and/or determined, in each case, at time points with a defined temporal spacing from one another. The defined temporal spacing can comprise, for example, one hour, 30 minutes, 15 minutes, 10 minutes, 5 minutes, 1 minute, 30 seconds. The plurality of the second data transfer rates thus describes a temporal variation of the data transfer rate. In particular, in the method step of determining the first data transfer rate, the first data transfer rate is determined on the basis of this temporal variation. In particular, the first data transfer rate can be extrapolated on the basis of the temporal variation. In other words, the prediction can be based upon an extrapolation.

The inventors have discovered that the first data transfer rate at the time point of the transfer of the first image dataset can be derived from the plurality of second data transfer rates. In other words, the inventors have discovered that the first data transfer rate can be derived from typical data transfer rates before the time point of the transfer.

According to at least one example embodiment, the first data transfer rate is predicted by applying a first trained function to the plurality of second data transfer rates.

In other words, in the method step of determining the first data transfer rate, the first data transfer rate is predicted and/or determined by applying the first trained function to the plurality of second data transfer rates.

In general, a trained function emulates cognitive functions that link humans to human thinking. In particular, by way of training based upon training data, the trained function can adapt to new circumstances and can recognize and extrapolate patterns.

In general, parameters can be adapted to a trained function by training. In particular, for this purpose, a supervised training, a semi-supervised training, an unsupervised training, a reinforcement learning and/or an active learning can be used. Furthermore, representation learning, also known using an alternative expression as "feature learning", can be used. In particular, the parameters of the trained functions can be adapted iteratively by way of a plurality of training steps.

In particular, a trained function can comprise a neural network, a support vector machine, a random tree or a decision tree and/or a Bayesian network, and/or the trained function can be based upon k-means clustering, Q-learning, genetic algorithms and/or association rules. In particular, a trained function can comprise a combination of a plurality of uncorrelated decision trees and/or an assembly of decision trees (a random forest). In particular, the trained function can be determined by XGboosting (Extreme Gradient Boosting). In particular, a neural network can be a deep neural network, a convolutional neural network or a convolutional deep neural network. Furthermore, a neural network can be an adversarial network, a deep adversarial network and/or a generative adversarial network. In particular, a neural network can be a recurrent neural network. In particular, a recurrent neural network can be a network with long short-term memory (LSTM), in particular, a gated recurrent unit (GRU). In particular, a trained function can comprise a combination of the described approaches. In particular, the approaches described here are specified for a trained function network architecture of the trained function.

The first trained function can be trained with the aid of training input data and training output data. The training input data can comprise a plurality of second training data transfer rates. The plurality of second training data transfer rates can have been determined and/or measured, in particular, for a timespan before a time point in the past. The training output data comprises a first training data transfer rate which has been determined and/or measured at the time point in the past. For training the first trained function, the first trained function is applied to the training input data, wherein a result is generated. The result is compared with the training output data. The first trained function is adapted such that the result matches as well as possible with the training output data. In particular, the training can be carried out by a plurality of training input data and training output data.

The inventors have discovered that the first data transfer rate on the basis of the plurality of second transfer rates can be determined by applying the first trained function. The inventors have discovered that with the aid of the first trained function, the first data transfer rate can be predicted.

According to at least one example embodiment, the first image dataset comprises at least one medical image of an examination object. In this context, the transfer parameter value comprises an information item concerning a movement of the examination object and/or an instrument situated within the examination object, relative to the medical technology device.

The examination object can be, in particular, a person or a patient. Alternatively, the examination object can be an animal or an object. The examination object can be, in particular, a portion, for example an organ, a limb, etc., of a person and/or an animal and/or an object. The instrument situated in the examination object can be, in particular, a catheter or an endoscope. Alternatively, the instrument situated in the examination object can be a surgical instrument, for example, a scalpel, a suction device and/or a swab, etc.

The at least one medical image can be, for example, an X-ray image, an ultrasound image and/or a slice image from a magnetic resonance tomography, a computed tomography and/or an angiography, etc. Alternatively, the medical image can comprise a three-dimensional representation of the examination object and/or the instrument. The medical image can be configured, in particular, as described above. At least a portion of the image values of the medical image can represent the examination object. Alternatively or additionally, at least a portion of the image values can represent the instrument. In other words, the medical image comprises a mapping of the examination object and/or the instrument.

The examination object can be positioned, in particular, in the medical technology device. In this context, the examination object can be positioned, for example, on a couch or patient table in the medical technology device. In this context, the examination object is positioned in the medical technology device such that the first image dataset captured with the medical technology device comprises a mapping of at least a portion of the examination object.

The movement of the examination object and/or the instrument relative to the medical technology device can be designated, in particular, a relative movement. In particular, in this context the medical technology device and/or the examination object and/or the instrument can move. In this context, the movement can be visible in the first image dataset and/or in the medical image. In other words, the movement of the examination object and/or the instrument relative to the medical technology device can be imaged and/or mapped. Alternatively or additionally, the relative movement can be represented and/or mapped in a plurality of medical images. In particular, the plurality of medical images can be included in the first image dataset. In this context, the plurality of medical images can image the sequence of medical images.

The relative movement of the examination object can be caused by a movement of the examination object. Alternatively or additionally, the relative movement of the examination object can be caused by a movement of the medical technology device relative to the examination object. For example, during an imaging by a C-arm system, the relative movement of the examination object can be caused by a movement of the examination object itself, a movement of the C-arm and/or a movement of the patient table. A movement of the patient table is also designated below a movement of the medical technology device.

The relative movement of the instrument can be caused by a movement of the instrument itself, a movement of the examination object itself or a movement of the medical technology device.

The inventors have discovered that the relative movement of the examination object can limit the relevant image information in particular cases. The inventors have discovered that this limit can be provided by the transfer parameter value and can be taken into account during capture of the first image dataset.

According to at least one example embodiment, the information concerning the relative movement of the examination object and/or the instrument in the medical image comprises an information item concerning the type of the relative movement and/or an information item concerning a velocity of the relative movement.

The information concerning the type of the relative movement specifies, in particular, whether the examination object itself, the instrument itself or the medical technology device moves. In other words, the information concerning the type of the relative movement states how the relative movement is caused. In other words, the information concerning the type of the relative movement states which object causes the movement of the examination object and/or the instrument relative to the medical technology device. In this context, the object can comprise the examination object, the instrument and/or the medical technology device. If a plurality of the objects move and/or if a plurality of the objects cause the relative movement, the information concerning the type of the relative movement can state all the objects that cause the relative movement. A relative movement that is caused by a plurality of objects can be designated an overlaid movement.

The information concerning the velocity of the relative movement states how rapidly the examination object and/or the instrument moves relative to the medical technology device. In particular, the information concerning the velocity of the relative movement can also state how rapidly the object which causes the movement actually moves. In the case of an overlaid movement, the individual velocity of each object which contributes to the relative movement can be included by the information concerning the relative movement of the examination object and/or the instrument. Alternatively or additionally, the information concerning the velocity of the relative movement can comprise a velocity of the overlaid movement.

Alternatively or additionally, the information concerning the relative movement of the examination object and/or the instrument can comprise an information item concerning a direction of the relative movement and/or a duration of the relative movement.

The information concerning the direction of the relative movement can comprise a direction of the movement of the examination object and/or the instrument relative to the medical technology device. Alternatively or additionally, the information concerning the direction of the relative movement in an overlaid movement can comprise an information item concerning an individual direction of the movement of each object which contributes to the overlaid movement. In particular, the information concerning the direction of the relative movement in an overlaid movement can comprise an information item concerning a direction of the overlaid movement.

The information concerning the duration of the relative movement can comprise an information item concerning how long the examination object and/or the instrument has already been moving relative to the medical technology device. Alternatively or additionally, the information concerning the duration of the relative movement can comprise an information item concerning a predicted duration of the movement of the examination object and/or the instrument relative to the medical technology device. Alternatively or additionally, the information concerning the duration of the relative movement in an overlaid movement can comprise an information item concerning the duration of the individual movement for each object which contributes to the overlaid movement.

The inventors have discovered that the relevant image information can depend upon the type of the relative movement and/or the velocity of the relative movement and/or can be limited thereby. In particular, a movement of the medical technology device can lead thereto that less image information is relevant, since the image information is used solely for positioning the medical technology device relative to the examination object. In particular, a movement of the instrument can mean that as much image information as possible is relevant since, with the instrument, for example, the medical intervention and/or the surgical operation is carried out and thus the image dataset is to be temporally and/or spatially resolved as highly as possible.

According to at least one example embodiment, the method step of determining the transfer parameter value also comprises a method step of determining the information concerning the relative movement of the examination object and/or the instrument.

In the method step of determining the information concerning the relative movement of the examination object and/or the instrument, in particular, the information concerning the type of the relative movement and/or the information concerning the velocity of the relative movement can be determined. Alternatively or additionally, the information concerning the direction of the relative movement and/or the duration of the relative movement can be determined.

In particular, the determination of the information concerning the relative movement can be based upon an image analysis of an image dataset captured before the first image dataset. In this context, the image dataset can be analyzed by an image analysis of a relative movement of the examination object and/or the instrument. On the basis of this image analysis, the information concerning the relative movement can be predicted for a time point of the capture of the first image dataset.

Alternatively or additionally, the information concerning the relative movement can be received in the method step of determining the information concerning the relative movement. In particular, an information item concerning a movement of the medical technology device and/or the instrument can be provided by the medical technology device and/or by the instrument and/or by a member of staff, to be received. The member of staff can be on site at the medical technology device. The member of staff can observe, in particular, the movement of the examination object and/or the instrument and/or the medical technology device. In particular, the member of staff can recognize which object or objects move. The member of staff can provide the information concerning the relative movement. Alternatively, the information concerning the relative movement can be derived from an information item provided by the member of staff regarding the movement of the examination object and/or the medical technology device and/or the instrument. Alternatively or additionally, it can be derived from the information provided by the medical technology device and/or from the information provided by the instrument which object and/or objects cause the relative movement. In particular, from the information provided by the medical technology device and/or by the instrument, the information concerning the relative movement of the examination object and/or the instrument can be derived.

The inventors have discovered that the information concerning the relative movement of the examination object and/or the instrument can be derived from observations by a member of staff and/or from information items provided. In particular, the information concerning the relative movement can be determined.

According to at least one example embodiment, the method step of determining the information concerning the relative movement of the examination object and/or the instrument comprises a method step of determining an information item concerning a movement of the medical technology device for a time point of a capture of the first image dataset. In this context, the information concerning the relative movement of the examination object and/or the instrument depends upon the movement of the medical technology device.

In the method step of determining the movement of the medical device, it is determined whether and how the medical technology device moves at the time point of the capture of the first image dataset. The information concerning the movement of the medical technology device can comprise, in particular, an information item concerning whether the medical technology device moves. Alternatively or additionally, the information concerning the movement of the medical technology device can comprise an information item concerning the velocity and/or the direction and/or the duration of the movement of the medical technology device. In particular, the information concerning the movement of the medical technology device can be provided by the medical technology device. Alternatively or additionally, the information concerning the movement of the medical technology device can be observed by the member of staff. In this context, the information concerning the movement of the medical technology device can be received.

In this context, the information concerning the relative movement of the examination object and/or the instrument depends upon the information concerning the movement of the medical technology device. In particular, the information concerning the relative movement of the examination object and/or the instrument can comprise the information concerning the movement of the medical technology device. In particular, the relative movement of the examination object and/or the instrument can correspond to the movement of the medical technology device if the examination object itself and/or the instrument itself do not move. The information concerning the type of movement can comprise, in particular, the information concerning whether the medical technology device moves.

The inventors have discovered that the information concerning the movement of the medical technology device is relevant for determining the relevant image information items. In other words, the relevant image information items depend upon the movement of the medical technology device. The inventors have discovered that fewer image information items are relevant if the medical technology device moves. In particular, the spatial and/or temporal resolution can be reduced. In addition, the inventors have discovered that by the information concerning the movement of the medical technology device, in the information concerning the relative movement of the examination object and/or the instrument, it is possible to distinguish between a movement of the examination object and/or the instrument and a movement of the medical technology device. In other words, it can be distinguished whether the medical technology device or the examination object and/or the instrument causes the relative movement. The inventors have discovered that this is important for determining which image information is relevant.

According to at least one example embodiment, the determination of the information concerning the movement of the medical technology device is based upon at least one device parameter value of the medical technology device and/or upon a measurement value of at least one sensor arranged on the medical technology device.

In other words, the information concerning the movement of the medical technology device can be derived from the at least one device parameter value and/or the measurement value of the sensor.

The at least one device parameter value can be configured to control a movement of the medical technology device.

The device parameter value can comprise, in particular, a velocity of the movement of the medical technology device and/or a direction of the movement of the medical technology device and/or a distance that the medical technology device covers with the movement. The device parameter value can be predetermined dependent upon the medical intervention and/or the progress of the medical intervention. Alternatively or additionally the device parameter value can be predetermined manually, for example, by the medical practitioner or the member of staff. In particular, the information concerning the movement of the medical technology device can be derived from the device parameter value.

The sensor is configured to capture and/or measure the movement of the medical technology device. In this context, the sensor is arranged on the medical technology device such that it can capture and/or measure the movement of the medical technology device. The sensor can comprise, in particular, a movement sensor and/or an acceleration sensor. The movement sensor can be configured, in particular, to capture a movement of the medical technology device. In particular, the movement sensor can capture whether the medical technology device moves and/or at what velocity the medical technology device moves. The acceleration sensor can capture, in particular, an acceleration during a movement of the medical technology device. It can be derived therefrom whether the medical technology device moves and/or at what velocity the medical technology device moves. Alternatively or additionally, from the measurement of the acceleration sensor, it can be derived in which direction the medical technology device moves. In particular, the information concerning the movement of the medical technology device can be derived from the movement of the medical technology device captured by the sensor.

The inventors have discovered that the movement of the medical technology device can be measured by at least one sensor. The inventors have discovered that alternatively or additionally, the information concerning the movement of the medical technology device can be derived from the device parameter value. In other words, the inventors have discovered that the medical technology device itself can provide the information concerning the movement of the medical technology device.

According to at least one example embodiment, in the method step of determining the information concerning the movement of the medical technology device, the information concerning the movement of the medical technology device can be derived from an examination protocol.

The examination protocol can describe the medical intervention. In particular, the examination protocol can describe when and/or how the first image dataset is to be captured during the medical intervention. In particular, the examination protocol can describe which position the medical technology device should assume, relative to the examination object, at which time point during the medical technology intervention. In particular, the examination protocol can specify at which time point during the medical intervention the medical technology device should assume the relevant position. The examination protocol can specify at what velocity the medical technology device should move, in particular, at the time point of the capture of the first image dataset. In particular, the examination protocol can specify the at least one device parameter value. In particular, the examination protocol can specify the movement of the medical technology device during the medical intervention. Thus, on the basis of the examination protocol, the movement of the medical technology device at the time point of the capture of the first image dataset can be predicted.

The information concerning the movement of the medical technology device can be derived, in particular, from the examination protocol and/or can be determined on the basis of the examination protocol.

The inventors have discovered that the information concerning the movement of the medical technology device can be determined on the basis of the examination protocol. The inventors have discovered that the examination protocol specifies the movement of the medical technology device during a medical intervention. The inventors have discovered that, on the basis of the examination protocol, the movement of the medical technology device for the time point of the capture of the first image dataset can be predicted.

According to at least one example embodiment, in the method step of determining the information concerning the relative movement of the examination object and/or the instrument, the information concerning the relative movement of the examination object and/or the instrument is determined by an edge analysis in the at least one first image dataset.

In particular, the edge analysis is applied to the at least one medical image included by the first image dataset. In particular, the edge analysis describes a form of the image analysis. In particular, by the edge analysis, a blurring of the edges in the first image dataset can be determined. In particular, from the blurring, the direction of the relative movement can be derived. In this context, edges which are oriented perpendicularly to the direction are more strongly blurred than edges that are oriented parallel to the direction. In addition, the velocity of the relative movement can be derived from a width and/or intensity of the blurring. The more strongly the edge is blurred, the faster the relative movement was at the time point of the capture of the first image dataset and/or the medical image.

For pixel data, the edge analysis can comprise, for example, one of the following operators: Sobel operator, Scharr operator, Laplace filter and/or Laplace operator, Prewitt operator, Roberts operator, Kirsch operator, Canny algorithm, Marr-Hildreth operator and/or Laplacian of Gaussian (LoG) and/or Mexican hat filter, contrast enhancer, active contour, extreme span filter. In particular, the first image dataset and/or the first medical image can comprise a plurality of pixels in a pixel matrix. In this context, an image value to which the relevant operator is applied can be associated with each pixel. In particular, it can then be analyzed how many pixels each edge comprises in the direction perpendicular to the edge. Therefrom, the intensity and/or the direction of the blurring can be determined.

In particular, the edge analysis can be applied to a first medical image included by the first image dataset. In this way, the information concerning the relative movement can be determined. The relative movement is included by the transfer parameter value. In particular, based thereon, the imaging parameter value can be determined for capturing the subsequent medical images that are included in the first image dataset. In particular, the image acquisition frequency can be determined on the basis of the information concerning the relative movement. In this context, a temporal spacing between the capture of the first medical image and a second medical image included by the first image dataset can be increased if a movement is recognized in the first medical image on the basis of the edge analysis. In this context, the first image dataset can comprise a temporal sequence of medical images. In other words, the information concerning the relative movement at the time point of the capture of a medical image of the sequence can be predicted and/or determined on the basis of the edge analysis in a previously captured medical image of the sequence.

The inventors have discovered that the information concerning the relative movement of the examination object and/or the instrument can be derived directly from the first image dataset. In particular, in this context, the edge analysis can be applied as a method of image analysis.

According to at least one example embodiment, the determination of the information concerning the relative movement of the examination object and/or the instrument is based upon at least one second image dataset.

In particular, the second image dataset is configured similarly to the first image dataset. In this context, the first and the second image dataset are captured at different time points. In particular, the second image dataset is captured before the first image dataset. In this context, the second image dataset comprises a medical image of the examination object and/or the instrument. In particular, the information concerning the relative movement can be derived from a comparison of the first and second image datasets. In particular, the examination object and/or the instrument can be displaced between the medical images included by the image datasets. In particular, the information concerning the relative movement can be derived from this displacement. In particular, from the displacement and the temporal spacing between the capture of the two image datasets, the velocity of the relative movement can be derived. In particular, from the displacement, the direction of the relative movement can be derived by taking account of the sequence during capture of the two image datasets.

In an alternative embodiment, the first image dataset can comprise a first and a second medical image. In this context, in the description above concerning determination of the relative movement, the first medical image can correspond to the first image dataset and the second medical image can correspond to the second image dataset. In particular, therefore, on the basis of the first and the second medical image, the relative movement of the examination object and/or the instrument can be derived. In other words, the information concerning the relative movement can be based upon the first and second medical image.

Alternatively, on the basis of an edge analysis of the second image dataset, as described above, a relative movement can be determined at the time point of the capture of the second image dataset. On the basis thereof, the relative movement at the time point of the capture of the first image dataset can be determined and/or derived and/or predicted. In particular, for example, a linear movement between the time points of the capture of the second and the first image datasets can be assumed.

The inventors have discovered that by an image analysis of the first and/or second image dataset, a displacement of the examination object and/or the instrument between the two image datasets can be determined and/or predicted. Furthermore, the inventors have discovered that, from this displacement, the information concerning the relative movement of the examination object and/or the instrument can be derived.

According to at least one example embodiment, in the method step of determining the information concerning the relative movement of the examination object and/or the instrument, the information concerning the relative movement of the examination object and/or the instrument is predicted by applying a second trained function to the at least one second image dataset.

In particular, the information concerning the relative movement of the examination object and/or the instrument at the time point of the capture of the first image dataset can be predicted by applying the second trained function to the plurality of second image datasets. In this context, the plurality of second image datasets is captured before the first image dataset.

The second trained function can in this context be configured, in particular, similarly to the first trained function as described above. In particular, the training of the second trained function can be configured similarly to the training of the first trained function. In this context, the first and the second trained functions differ, in particular, with regard to the training input data and the training output data. The training input data for the second trained function can comprise, in particular, at least one second training image dataset. In particular, the training input data can comprise a plurality of second training image datasets. The training output data can then comprise the training information concerning a relative movement of an examination object and/or an instrument in a first training image dataset. In this context, the at least one second training image dataset is captured before the first training image dataset. The training information items regarding the relative movement can have been determined, in particular, manually on the basis of the first training image dataset.

The inventors have discovered that the information concerning the relative movement of the examination object and/or the instrument can be determined by applying the second trained function to at least one second image dataset captured in advance. In particular, it is possible to predict the information concerning the relative movement for the time point of the capture of the first image dataset.

According to at least one example embodiment, the imaging parameter value comprises at least one value for one of the following parameters: dose, image acquisition frequency, binning.

The dose states what dose quantity is applied to the examination object during the capture of the first image dataset. A lower dose can lead to a lower spatial resolution. In particular, a reduction in the dose leads to a reduction in the signal-to-noise ratio in the first image dataset. In particular, the dose is given in relation to X-ray radiation. The dose can be given, in particular, in gray (Gy) or sievert (Sv). The dose can depend, in particular, on an acquisition time, an X-ray voltage or a tube voltage and/or an X-ray current or tube current for generating the X-ray radiation.

The image acquisition frequency gives a temporal spacing between the capture of two medical images. In this context, a first medical image can be included by the first image dataset and a second medical image can be included by the second image dataset. The first and second medical image are captured directly one after the other. In this case, the image acquisition frequency can also describe and/or state and/or include the temporal spacing between two image datasets. Alternatively, the first and the second medical image can be included by the first image dataset. In this context, the first and the second medical image are captured directly one after the other. The image acquisition frequency then describes the temporal spacing of the medical images of the first image dataset. In particular, the image acquisition frequency specifies the temporal resolution. The image acquisition frequency can be specified, in particular, in recordings per second.

The binning specifies, in particular, a spatial resolution of a detector. The detector can be configured, in particular, to capture the first image dataset. The detector can be an X-ray detector for detecting X-ray radiation. The detector can be, for example, a scintillation detector or a semiconductor detector. In particular, the detector can be a pixelated detector. In other words, the detector can comprise a pixel matrix. In this context, the detector can capture an image value for each pixel. The image values are represented in the medical image and/or in the first image dataset. The binning specifies how many pixels form a binned pixel. In the case of a binned pixel, a plurality of pixels are grouped together to a large pixel. By this, the spatial resolution is reduced. Furthermore, through the binning, a data quantity included by the corresponding image dataset or medical image is reduced. By the binning, a sensitivity of the detector can be increased. With a higher sensitivity, in particular, a lower dose is necessary in order to capture the medical image or the first image dataset. The medical image and/or the first image dataset in this context includes the binned pixels. In other words, the medical image and/or the first image dataset includes an image value for each binned pixel. The image value of the binned pixel can correspond to the sum or the mean value or the median of the captured image values of the pixels included by the binned pixels. For example, a binning of 1×1 or 2×2 or 4×4 or 16×16 can be selected.

The inventors have discovered that these imaging parameter values are suitable for adapting the spatial and/or temporal resolution of the first image dataset so that the first image dataset comprises only the relevant image information items. In particular, by way of an adaptation of these imaging parameter values, a radiation load or an applied dose can be varied and/or adapted.

According to at least one example embodiment, the method also comprises a method step of capturing the first image dataset dependent upon the imaging parameter value. The method further comprises a method step of transferring the first imaging dataset from the medical device to the remotely arranged device.

In the method step of capturing the first image dataset, the first image dataset is captured with the medical device. In this context, the medical device is controlled by the imaging parameter value. In other words, the imaging parameter value specifies at least partially how the first image dataset is captured with the medical device.

In the method step of transferring the first image dataset, the first image dataset is transferred from the medical device to the remotely arranged device. In particular, the first image dataset is transferred as described above. In particular, the first image dataset can be transferred via an LAN or a WLAN and/or via a mobile communications network.

The inventors have discovered that the first image dataset can be transferred directly without lossy compression if it was captured on the basis of the transfer parameters.

According to at least one example embodiment, the first image dataset comprises a temporal sequence of medical images comprising a first and a second medical image. In this context, the second image is captured before the first image. A transferred image information item of the first medical image is based upon a transferred image information item of the second medical image.

The temporal sequence comprises at least the first and the second medical image. In particular, the temporal sequence can comprise more than two medical images. The medical images are captured separated temporally from one another. The medical images of the sequence are therefore sorted temporally. In other words, the medical images include a sequence. In this context, the second medical image is arranged temporally before the first medical image. When the first medical image is transferred, only the part of the first medical image which comprises an image information item that is different from the image information item included by the first medical image is transferred. On the remotely arranged device, the transferred image information of the first medical image can be combined with the already known image information item of the second medical image in order to represent the entire image information item of the first medical image.

Alternatively, the first medical image can be included by the first image dataset and the second medical image can be included by the second image dataset. In particular, the transfer of the image information can take place as described above.

The inventors have discovered that in this way, the transferred data quantity can be minimized. The inventors have discovered that in this way, the transfer can be accelerated. The inventors have discovered that, in this way, a lower data transfer rate is needed and costs can therefore be saved.

According to at least one example embodiment, the medical technology device is based upon imaging by X-ray radiation. In this context, dependent upon the transfer parameter value, a collimator is used.

In this context, the medical technology device can be, in particular, an X-ray system, an angiography system or a C-arm system. The medical technology device in this context comprises an X-ray tube and an X-ray detector. In this context, the X-ray tube and the X-ray detector are arranged such that an X-ray radiation emitted by the X-ray tube is detected by the X-ray detector. In order to capture an image dataset from the examination object, the examination object is positioned between the X-ray tube and the X-ray detector so that it is penetrated by the X-ray radiation. In this context, as far as possible, only as much X-ray radiation should penetrate the examination object so that the captured image dataset comprises the relevant image information. The collimator can be positioned in front of the X-ray tube. The collimator is configured so that it absorbs X-ray radiation which then no longer penetrates the examination object. The collimator can be made, in particular, of lead. The collimator can be formed, in particular, wedge-shaped in the radiation direction. In other words, the collimator can be thicker on one side than on the other side in the radiation direction. If the transfer parameter comprises an information item concerning a relative movement, the collimator can be used dependent upon the movement. In particular, if the information concerning the direction of the relative movement is included by the information concerning the relative movement, the wedge-shaped collimator can be used such that the thicker part of the collimator points away from the direction of the relative movement.

The inventors have discovered that it can be assumed that image information items that are captured from a region of the examination object that is moved out of the first image dataset by the relative movement are not relevant. In order to apply as small a dose as possible, this region can be screened from the X-ray radiation by the collimator.

At least some example embodiments further relate to a determining system for determining an imaging parameter value for the control of a medical technology device during a capture of a first image dataset. In this context, the first image dataset is provided to be transferred from the medical technology device to a remotely arranged device. The determining system comprises an interface and a computing unit. In this context, the interface and/or the computing unit is configured for receiving and/or determining the transfer parameter value. In this context, the transfer parameter value comprises an information item concerning which image information is relevant for the first image dataset which is to be transferred. In this context, the computing unit is also configured for determining the imaging parameter value dependent upon the transfer parameter value. In this context, the interface is also configured for providing the imaging parameter value.

A determining system of this type can be configured, in particular, to carry out the method described above for determining an imaging parameter value for the control of a medical technology device during a capture of a first image dataset and its aspects. The determining system is configured to carry out this method and its aspects in that the interface and the computing unit are configured to carry out the corresponding method steps.

At least some example embodiments relate to a computer program product having a computer program, and also a computer-readable medium. A realization largely through software has the advantage that conventionally used determining systems can also easily be upgraded by way of a software update in order to operate in the manner described. Where relevant, apart from the computer program, such a computer program product can comprise additional constituents, such as, for example, documentation and/or additional components as well as hardware components, for example, hardware keys (dongles, etc.) for using the software.

At least some example embodiments relate, in particular, to a computer program product with a computer program which is directly loadable into a memory store of a determining system, having program portions in order to carry out all the steps of the method described above for determining an imaging parameter value for the control of a medical technology device during a capture of a first image dataset and its aspects when the program portions are executed by the determining system.

In particular, At least some example embodiments relate to a computer readable storage medium on which program portions readable by a determining system are stored in order to carry out all the steps of the method described above for determining an imaging parameter value for the control of a medical technology device during a capture of a first image dataset and its aspects when the program portions are executed by the determining system.

FIG. 1 shows a first exemplary embodiment of a method for determining an imaging parameter value for the control of a medical technology device during a capture of a first image dataset.

The medical technology device is an imaging medical technology device. In other words, the medical technology device is configured to capture an image dataset. In this context, the medical technology device is configured, in particular, to capture the first image dataset. In this exemplary embodiment, the medical technology device is an angiography system. Alternatively, the medical technology device can be a C-arm system, a computed tomography system, a magnetic resonance tomography system, an ultrasound system and/or an optical coherence tomography system, etc.

The medical technology device can be controlled by the imaging parameter value. In this context, the imaging parameter value defines how the medical technology device is to capture the first image dataset. For example, the imaging parameter value can specify a dose and/or an exposure time and/or an image acquisition frequency and/or a binning, etc., during the capture of the first image dataset.

The first image dataset can comprise, in particular, a mapping of an examination object. In the exemplary embodiment, the first image dataset comprises at least one medical image. The medical image in this context represents the examination object. In particular, the first image dataset can comprise a temporal sequence of medical images. Alternatively, the first image dataset can itself be a medical image.

The medical image can be, in particular, a pixelated or a voxelated image. In other words, the medical image can comprise a pixel matrix or a voxel matrix. In this context, the pixel matrix and/or the voxel matrix comprises a plurality of pixels and/or voxels, wherein each pixel or voxel is associated with an image value. The image values represent the mapping of the examination object.

The examination object is in this context at least a part of a person, in particular a patient. The part of the patient can be, for example, an organ or a limb. Alternatively, the examination object can comprise an animal or a part of an animal or an object.

The first image dataset is configured to be transferred to a remotely arranged device. By the transfer, the first image dataset is available on the remotely arranged device. The remotely arranged device is in this context arranged remotely from the medical technology device. The remotely arranged device can be arranged in the same room as the medical technology device, spaced from the medical technology device. Alternatively, the remotely arranged device can be arranged in a different room and/or in a different building and/or in a different city and/or in a different country from the medical technology device. The first image dataset can in this context be transferred via a network, for example, via an LAN, a WLAN or a mobile communications network from the medical device to the remotely arranged device. In this context, the first medical dataset is to be transferred within a medically useful time interval. The medically useful time interval can comprise, for example, 500 ms or 1 s. If the first image dataset comprises a temporal sequence of medical images, the medically useful time interval can be no more than the temporal spacing between the capture of two medical images of the sequence.

At the remotely arranged device, a medical practitioner can monitor and/or carry out a medical intervention on the examination object making use of the first image dataset. For this purpose, the first image dataset is displayed to the medical practitioner by a display unit. If the first image dataset comprises more than one medical image, the medical images are displayed to the medical practitioner in a video sequence. In this regard, a medically useful time interval defines a time interval that does not delay and/or interrupt the medical intervention.

In a method step of receiving REC-1 and/or determining DET-1 a transfer parameter value, the transfer parameter is received, in particular, by an interface SYS.IF and/or is determined by a computing unit SYS.CU. In this context, the transfer parameter value comprises an information item concerning which image information is relevant for the first image dataset which is to be transferred.

In this context, in particular, the image information which can actually be transferred via the network is relevant. Image information items which could not be transferred due to a lossy compression are not relevant for the first image dataset. Non-transferred image information items cannot be provided for, in particular displayed to, the medical practitioner on the remotely arranged device. These image information items are therefore not relevant to the medical practitioner. Thus, the actually transferrable image information describes a limit for the relevant image information.

Alternatively or additionally, different image information items are relevant dependent upon a progress of the medical intervention. For example, the medical practitioner can position the medical device relative to the examination object on the basis of the first image dataset. In this context, a good spatial resolution and/or a good temporal resolution of the first image dataset is not necessary. The temporal resolution is in this context defined, in particular, by the number of pixels and/or voxels in the first medical image dataset. In addition, the spatial resolution can depend upon a signal-to-noise ratio. The temporal resolution depends, in a sequence of medical images, on the temporal spacing between the capture of two successive medical images, the image acquisition frequency. For positioning, after the transfer, interpolated medical images between the actually captured medical images can be determined and provided and/or displayed to the medical practitioner. When the medical intervention is carried out, a comparatively greater spatial and/or temporal resolution is relevant for the medical practitioner. More image information is therefore relevant herein than during positioning. In other words, the image information of interest to the medical practitioner can specify a limit for the relevant image information.

In the method step of receiving REC-1 the transfer parameter value, the transfer parameter value can be received, for example, from a database. Alternatively, the medical practitioner can provide the transfer parameter value. The transfer parameter value can be based in this context upon a progress of the medical intervention.

In the method step of determining DET-1 the transfer parameter value, the transfer parameter value can be determined, for example, on the basis of the progress of the medical intervention. Alternatively or additionally, the transfer parameter value can be determined on the basis of a current technical condition, for example, regarding the network.

In a method step of determining DET-2 the imaging parameter value, the imaging parameter value is determined dependent upon the transfer parameter value. The first image dataset can be captured with the medical device on the basis of the imaging parameter value.

In this context, the imaging parameter value is determined in such a way that the first image dataset comprises not more than the relevant image information. In other words, the imaging parameter value is determined in such a way that the first image dataset comprises only the image information that is relevant according to the limitation by the transfer parameter value. In other words, the imaging parameter value is determined in such a way that a quality of the first image dataset is limited by the relevant image information. In this context, the quality determines which image information the first image dataset comprises. The quality relates, for example, to the spatial resolution and/or the temporal resolution and/or the signal-to-noise ratio, etc. The object structures which are included by the image information of the first image dataset depend upon the spatial resolution and the signal-to-noise ratio, for example. The time scale changes in the first image dataset which can be observed depend upon the temporal resolution. This means that the temporal changes which are included by the image information depend upon the temporal resolution.

The imaging parameter value is thus determined such that no "non-essential" image information is captured that either cannot be transferred or is not of interest to the medical practitioner. Therefore, on the basis of the imaging parameter value, only the relevant image information is captured in the first image dataset.

In a method step of providing PROV-1 the imaging parameter value, the imaging parameter value is provided, in particular, by the interface SYS.IF. In particular, the imaging parameter value is provided for use by the medical device. In other words, the imaging parameter value is provided such that the medical device can be controlled with the imaging parameter value during capture of the first image dataset.

Figure 2:
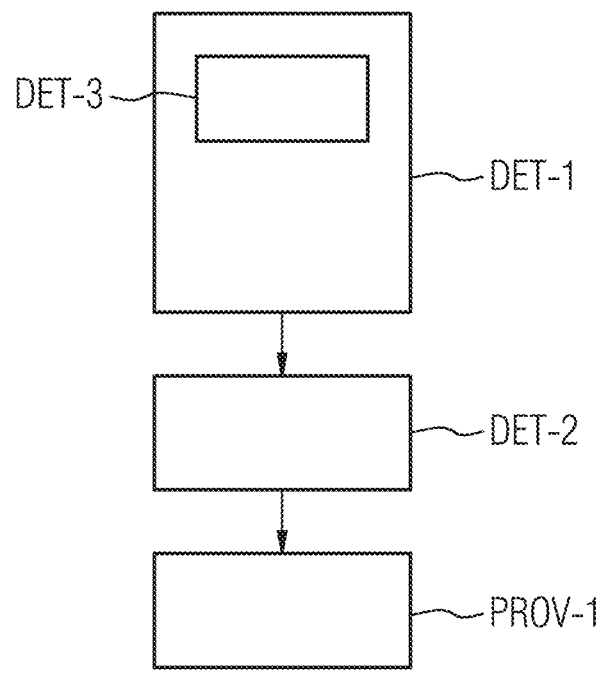
FIG. 2 shows a second exemplary embodiment of a method for determining an imaging parameter value for the control of a medical technology device during a capture of a first image dataset.

FIG. 2 shows a second exemplary embodiment of a method for determining an imaging parameter value for the control of a medical technology device during a capture of a first image dataset.

The method steps of determining DET-1 a transfer parameter value, determining DET-2 an imaging parameter value and providing PROV-1 can in this context be configured according to the description in relation to FIG. 1.

In an alternative embodiment, the exemplary embodiment shown here can also comprise the method step described in relation to FIG. 1 of receiving REC-1 a transfer parameter value. In particular, the received transfer parameter value can relate to a transfer parameter different from the determined transfer parameter value. For example, the received transfer parameter value can concern a transfer parameter relating to the network and the determined transfer parameter value can concern a transfer parameter relating to a progress of the medical intervention.

The transfer parameter value can, in particular, comprise a first data transfer rate. The first data transfer rate specifies a data quantity that can be transferred over the network in a particular time interval. In particular, the first data transfer rate specifies what data quantity can be transferred via the network at the time point of the transfer of the first image dataset. The time point of the transfer can comprise, in particular, a time interval. The first data transfer rate is typically specified in bits per second (bit/s). The first image dataset in this context comprises a data quantity that is transferred. The data quantity in this context depends, in particular, on the number of pixels and/or voxels included by the first image dataset and/or the medical image. On a transfer of the first image dataset via a 5G mobile communication network, the first data transfer rate can be pre-reserved. In particular, the pre-reserved first data transfer rate can be received as a transfer parameter value in the method step of receiving REC-1 the transfer parameter value.

Alternatively, the method step of determining DET-1 the transfer parameter value can comprise a method step of determining DET-3 the first data transfer rate for a time point of the transfer of the first image dataset.

In this context, the first data transfer rate can be determined on the basis of an experience of a member of staff. For example, a typical data transfer rate for different times of day and/or days of the week can be known to the member of staff and this can be used at the time point of the transfer of the first image dataset.

Alternatively, the first data transfer rate can be predicted on the basis of a plurality of second data transfer rates. In this context, the plurality of second data transfer rates is determined before the time point of the transfer of the first image dataset.

In particular, the plurality of the second data transfer rates can map a temporal variation of the data transfer rate of the network. On the basis of this temporal variation, the first data transfer rate can be determined by extrapolation.

Alternatively, the first data transfer rate is predicted by applying a first trained function to the plurality of second data transfer rates. The first trained function can in this context be configured as a long short-term memory (LSTM) network. The first trained function is trained such that, on the basis of a temporal variation of the data transfer rate in the past, it can predict the first data transfer rate in the future. For this purpose, the first trained function can be trained with measured data transfer rates from the past.

Figure 3:
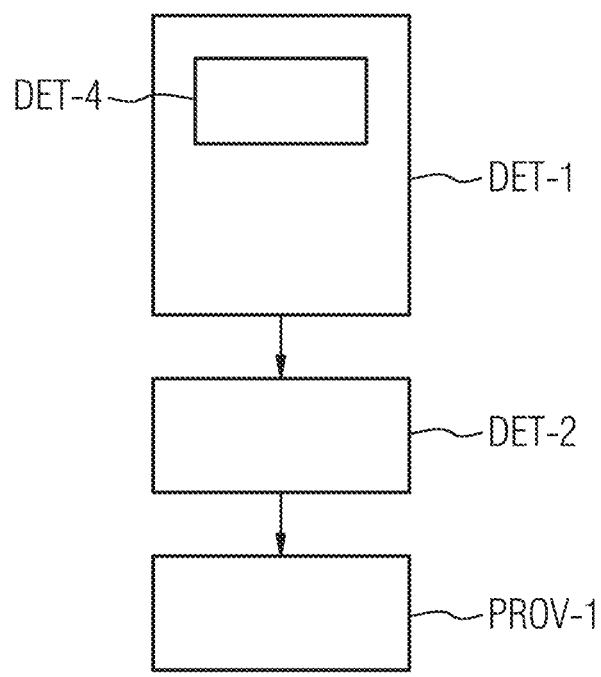
FIG. 3 shows a third exemplary embodiment of a method for determining an imaging parameter value for the control of a medical technology device during a capture of a first image dataset.

FIG. 3 shows a third exemplary embodiment of a method for determining an imaging parameter value for the control of a medical technology device during a capture of a first image dataset.

The method steps of determining DET-1 a transfer parameter value, determining DET-2 an imaging parameter value and providing PROV-1 can in this context be configured according to the description relating to FIG. 1.

In an alternative embodiment, the exemplary embodiment shown here can also comprise the method step described in relation to FIG. 1 of receiving REC-1 a transfer parameter value. In particular, the received transfer parameter value can relate to a transfer parameter different from the determined transfer parameter value. For example, the received transfer parameter value can concern a transfer parameter relating to the network and the determined transfer parameter value can concern a transfer parameter with respect to a progress of the medical intervention.

In this context, the transfer parameter value comprises an information item concerning a movement of the examination object and/or an instrument situated within the examination object relative to the medical technology device. In an embodiment as an alternative to this exemplary embodiment, the information concerning the relative movement can be received, for example, by the medical technology device and/or by a member of staff.

The instrument can be, in particular, a catheter or an endoscope. Alternatively or additionally, the instrument can be a scalpel, a swab, a retractor or other surgical instrument. The instrument can be configured for carrying out the medical intervention.

During the relative movement of the examination object, both the examination object itself and/or the medical technology device can move. During the relative movement of the instrument, the instrument itself, the examination object itself and/or the medical technology device can move. The relative movement can be an overlaid movement. During an overlaid movement, more than one object moves relative to one another. In this context, the moved objects can comprise the examination object and/or the instrument and/or the medical technology device.

The information concerning the relative movement of the examination object and/or the instrument can comprise, in particular, an information item concerning the type of the relative movement and/or an information item concerning a velocity of the relative movement.

The information concerning the type of the relative movement in this context specifies which object causes the relative movement. In other words, the information concerning the type of the relative movement specifies which object actually moves. In an overlaid movement, the information concerning the type of the relative movement specifies all the objects that actually move.

The information concerning the velocity comprises, in particular, the velocity of the relative movement. Alternatively or additionally, the information concerning the velocity can comprise the velocity of each object that causes the relative movement.

Alternatively or additionally, the information concerning the relative movement can comprise an information item concerning a direction of the relative movement and/or a duration of the relative movement. Herein also, the information can relate, in each case, to the relative movement overall and/or to the actual movement of the individual causative objects.

The method step of determining DET-1 the transfer parameter value comprises a method step of determining DET-4 the information concerning the relative movement of the examination object and/or the instrument.

The information concerning the relative movement can be determined, in particular, by an edge analysis in the at least one image dataset. In particular, the edge analysis can be carried out on the at least one medical image included by the first image dataset. The edge analysis can be carried out on a pixelated or voxelated medical image, in particular, by applying one of the following operators: Sobel operator, Scharr operator, Laplace filter and/or Laplace operator, Prewitt operator, Roberts operator, Kirsch operator, Canny algorithm, Marr-Hildreth operator and/or Laplacian of Gaussian (LoG) and/or Mexican hat filter, contrast enhancer, active contour, extreme span filter. In this context, the velocity of the relative movement can be determined, for example, from a width of an edge and/or from a blurring of the edge. Dependent upon which edges are blurred, the direction of the relative velocity can be determined. If the first image dataset comprises a sequence of medical images, then on the basis of an edge analysis of a second medical image, the information concerning the relative movement at the time point of the capture of a first medical image can be determined. In this context, the first medical image is determined temporally after the second medical image. In other words, the information concerning the relative movement for the time point of the capture of the first image can be predicted.

Alternatively or additionally, the determining DET-4 of the information concerning the relative movement of the examination object and/or the instrument can be based upon at least one second image dataset. The at least one second image dataset is in this context captured before the first image dataset. For the at least one second image dataset, the information concerning the relative movement can be determined. Based thereon, the information concerning the relative movement can be derived for the first image dataset. In other words, the information concerning the relative movement for the first image dataset can be predicted on the basis of the information concerning the relative movement for the at least one second image dataset. For example, a linear movement can be presupposed and it can be assumed that the information concerning the relative movement between the capture of the second and the first image datasets does not change. Alternatively, as described above for the first and second medical images, the information concerning the relative movement can be determined on the basis of an edge analysis of the second image dataset for the time point of the capture of the first image dataset.

Alternatively, the information concerning the relative movement of the examination object and/or the instrument can be determined by applying a second trained function to the at least one second image dataset. The second trained function can be configured similarly to the first trained function according to the description relating to FIG. 2. In particular, the second trained function can be applied to a plurality of second image datasets. In this context, the plurality of second image datasets is captured before the time point of capturing the first image dataset. The second trained function can be trained on the basis of image datasets from the past. In this context, the image datasets can be annotated manually on the basis of an observation.

Figure 4:
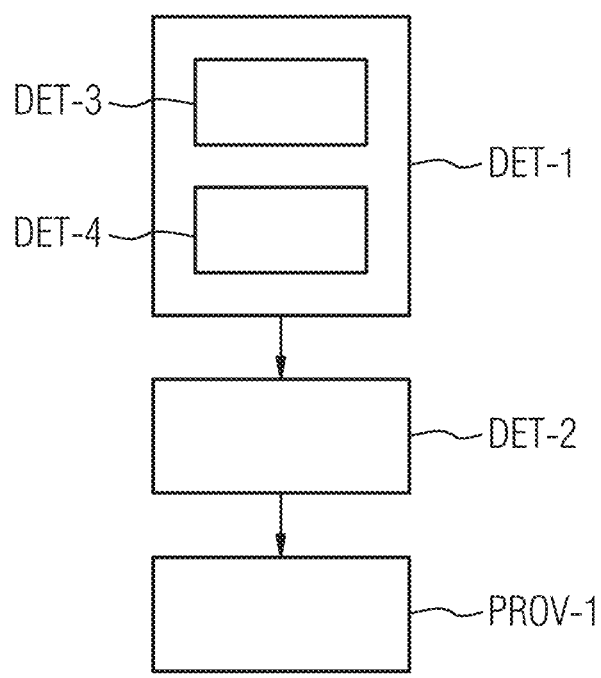
FIG. 4 shows a fourth exemplary embodiment of a method for determining an imaging parameter value for the control of a medical technology device during a capture of a first image dataset.

FIG. 4 shows a fourth exemplary embodiment of a method for determining an imaging parameter value for the control of a medical technology device during a capture of a first image dataset.

The method steps of determining DET-1 a transfer parameter value, determining DET-2 an imaging parameter value and providing PROV-1 can in this context be configured according to the description relating to FIG. 1.

In an alternative embodiment, the exemplary embodiment shown here can also comprise the method step described in relation to FIG. 1 of receiving REC-1 a transfer parameter value. In particular, the received transfer parameter value can relate to a transfer parameter different from the determined transfer parameter value. For example, the received transfer parameter value can concern a transfer parameter relating to the network and the determined transfer parameter value can concern a transfer parameter with respect to a progress of the medical intervention.

The method step of determining DET-3 the first data transfer rate is configured similarly to the description in relation to FIG. 2. The method step of determining DET-4 the relative movement of the examination object and/or the instrument is configured similarly to the description in relation to FIG. 3.

The method steps of determining DET-3 the first data transfer rate and of determining DET-4 the relative movement can in this context be carried out simultaneously or after one another in any desired sequence. The transfer parameter value determined in the method step of determining DET-1 the transfer parameter value can therefore comprise more than one parameter value. A parameter value of this type can be the first data transfer rate or the information concerning the relative movement.

Figure 5:
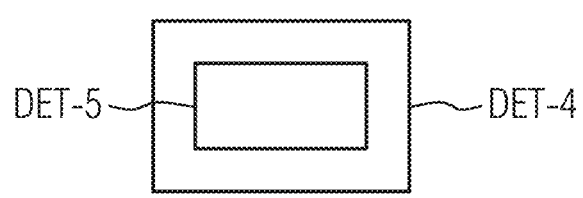
FIG. 5 shows an exemplary embodiment of a method step for determining an information item relating to a relative movement of an examination object and/or an instrument situated within the examination object.

FIG. 5 shows an exemplary embodiment of a method step for determining DET-4 an information item concerning a relative movement of an examination object and/or an instrument situated within the examination object.

The exemplary embodiment described below can be combined, in particular, with the exemplary embodiments according to FIGS. 3 and 4. The information concerning the relative movement is in this context configured as described in the description relating to FIG. 3.

The method step of determining DET-4 the information concerning the relative movement comprises a method step of determining DET-5 an information item concerning a movement of the medical technology device for a time point of a capture of the first image dataset. In this context, the information concerning the relative movement of the examination object and/or the instrument depends upon the movement of the medical technology device. In this context, the information concerning the relative movement can comprise the information concerning the movement of the medical technology device. In addition, the information concerning the relative movement can comprise information items that have been derived from the information concerning the movement of the medical technology device. For example, on the basis of the edge analysis, a relative movement of the examination object can be determined. In combination with the information concerning the movement of the medical technology device, it can be derived therefrom which type of movement is concerned (movement of the examination object and/or movement of the medical technology device) and which object causing the relative movement moves, and how fast.

The determination DET-5 of the information concerning the movement of the medical technology device can in this context be based upon at least one device parameter value of the medical technology device and/or upon a measurement value of at least one sensor arranged on the medical technology device.

The at least one device parameter value is in this context configured to control the medical technology device. In particular, the device parameter value is configured to control a movement of the medical technology device. The device parameter value can specify, for example, a velocity, a direction and/or a target position for the movement of the medical technology device. Through the movement of the medical technology device, the specifications of the device parameter values can be fulfilled. On the basis of the device parameter value, in particular, the velocity and/or the direction and/or the duration of the movement of the medical technology device can be derived and/or determined. In particular, on the basis of the device parameter value, it can be determined whether the medical technology device moves. Thus, the information concerning the type of the relative movement can be determined on the basis of the device parameter value. The device parameter can be received, in particular, from the medical device.

The at least one sensor can be configured, in particular, as a movement sensor and/or as an acceleration sensor. The movement sensor can in this context be configured, in particular, to capture a movement, in particular, a velocity of the movement of the medical technology device. The acceleration sensor can in this context be configured to capture a movement, in particular, a direction and/or a velocity of the movement of the medical technology device. In particular, the movement sensor and/or the acceleration sensor can be configured to detect whether the medical technology device moves. As described above in relation to the device parameter value, the information concerning the relative movement can be derived and/or determined on the basis of the measurement value. The measurement value can, in particular, be received.

In particular, on the basis of a device parameter value and/or a measurement value which was determined and/or received before the time point of the capture of the first image dataset, the information concerning the movement of the medical technology device at the time point of the capture of the first image dataset can be predicted.

Alternatively or additionally, in the method step of determining DET-5 the information concerning the movement of the medical technology device, the information concerning the movement of the medical technology device can be derived from an examination protocol.

The examination protocol can specify and/or comprise, in particular, a sequence of the medical intervention. In this context, the examination protocol can specify when the first image dataset is captured. Alternatively or additionally, the examination protocol can specify how the medical technology device is to be moved at which time point and/or how it is to be positioned. In particular, the at least one device parameter value can be specified and/or included in the examination protocol. On the basis of the examination protocol, the information concerning the movement of the medical technology device at the time point of the capture of the first image dataset can be predicted. As described above, the information concerning the relative movement can be derived and/or determined on the basis of the information concerning the movement of the medical technology device.

Figure 6:
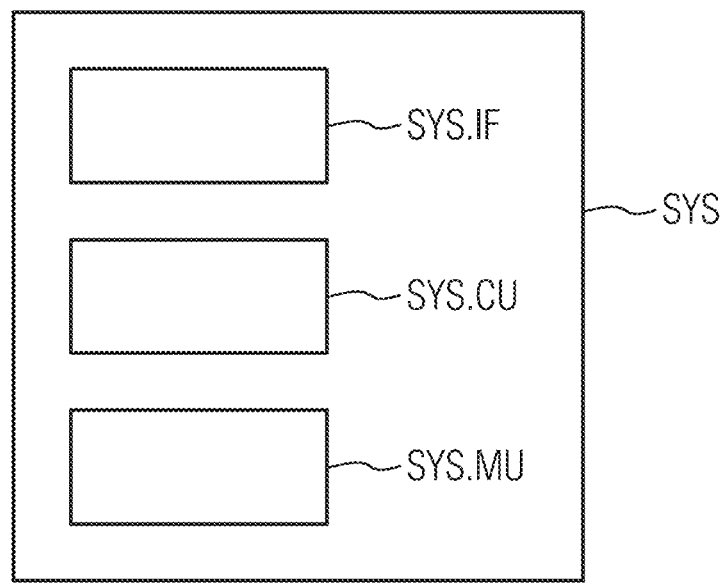
FIG. 6 shows a determining system for determining an imaging parameter value for the control of a medical technology device during a capture of a first image dataset.
Figure 7:
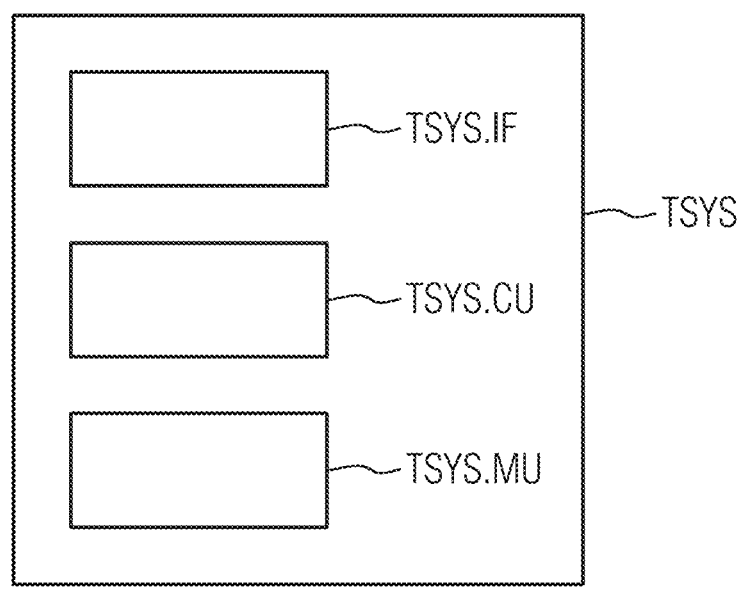
FIG. 7 shows a training system for providing a first or second trained function.

FIG. 6 shows a determining system SYS for determining an imaging parameter value for the control of a medical technology device during a capture of a first image dataset. FIG. 7 shows a training system TSYS for providing a first or second trained function.

The determining system SYS shown for providing is configured to carry out a method according to at least some example embodiments for determining an imaging parameter value for the control of a medical technology device during a capture of a first image dataset. The training system TSYS shown is configured to carry out a method according to at least some example embodiments for providing the first or second trained function. The determining system SYS comprises an interface SYS.IF, a computing unit SYS.CU and a memory unit SYS.MU. The training system TSYS comprises a training interface TSYS.IF, a training computing unit TSYS.CU and a training memory unit TSYS.MU.

The determining system SYS and/or the training system TSYS can be, in particular, a computer, a microcontroller or an integrated circuit (IC). Alternatively, the determining system SYS and/or the training system TSYS can be a real or virtual computer network (a technical term for a real computer network is a "cluster" and a technical term for a virtual computer network is a "cloud"). The determining system SYS and/or the training system TSYS can be configured as a virtual system which is executed on a computer or a real computer network or a virtual computer network (a technical term for this is "virtualization").

The interface SYS.IF and/or the training interface TSYS.IF can be a hardware or software interface (for example, a PCI bus, a USB or a Firewire). The computing unit SYS.CU and/or the training computing unit TSYS.CU can comprise hardware and/or software constituents, for example, a microprocessor or a so-called field-programmable array (FPGA). The memory unit SYS.MU and/or the training memory unit TSYS.MU can be realized as a non-permanent working memory (Random Access Memory, (RAM)) or as a permanent mass storage unit (hard disk, USB stick, SD card, solid state disk (SSD)).

The interface SYS.IF and/or the training interface TSYS.IF can, in particular, comprise a plurality of sub-interfaces which carry out different method steps of the respective method according to at least some example embodiments. In other words, the interface SYS.IF and/or the training interface TSYS.IF can be configured as a plurality of interfaces SYS.IF and/or training interfaces TSYS.IF. The computing unit SYS.CU and/or the training computing unit TSYS.CU can comprise, in particular, a plurality of computer sub-units which carry out different method steps of the respective method according to at least some example embodiments. In other words, the computing unit SYS.CU and/or the training computing unit TSYS.CU can be configured as a plurality of computing units SYS.CU and/or training computing units TSYS.CU.

Where it has not yet explicitly been set out, but is useful and in the spirit of example embodiments, individual exemplary embodiments, individual sub-aspects or features thereof can be combined or exchanged with one another without departing from the scope of example embodiments. Advantages of example embodiments described in relation to an exemplary embodiment also apply, where transferrable, to other exemplary embodiments without this being explicitly stated.

The invention claimed is:

1. A computer-implemented method for determining an imaging parameter value for control of a medical technology device during a capture of a first image dataset, wherein the first image dataset is to be transferred from the medical technology device to a remotely arranged device, the method comprising:
   at least one of receiving or determining a transfer parameter value, wherein the transfer parameter value includes an information item concerning which image information is relevant for the first image dataset which is to be transferred;

determining the imaging parameter value based on the transfer parameter value; and providing the imaging parameter value, wherein the transfer parameter value includes a first data transfer rate, and determining the transfer parameter value includes determining the first data transfer rate for a time point of a transfer of the first image dataset by predicting the first data transfer rate by applying a first trained function to a plurality of second data transfer rates.

2. The method of claim 1, wherein the imaging parameter value is determined such that a quality of the first image dataset is limited by the image information.

3. The method of claim 1,
wherein the plurality of second data transfer rates is determined before the time point of the transfer of the first image dataset.

4. The method of claim 1, wherein the imaging parameter value comprises at least one value for at least one of dose, image acquisition frequency, or binning.

5. A non-transitory computer program product having a computer program which is directly loadable into a memory store of a determining system, the computer program having program portions that, when executed by the determining system, cause the determining system to perform the method of claim 1.

6. A non-transitory computer-readable storage medium having instructions, when executed by a determining system, configured to cause the determining system to perform the method of claim 1.

7. The method of claim 1, further comprising:
transferring the first imaging dataset from the medical technology device to the remotely arranged device.

8. A determining system for determining an imaging parameter value for control of a medical technology device during a capture of a first image dataset, wherein the first image dataset is to be transferred from the medical technology device to a remotely arranged device, the determining system comprising:

an interface; and a computing device, wherein at least one of the interface or the computing device is configured to at least one of receive or determining a transfer parameter value, the transfer parameter value comprises an information item concerning which image information is relevant for the first image dataset which is to be transferred, the computing device is also configured to determine the imaging parameter value based on the transfer parameter value, the interface is also configured to provide the imaging parameter value, the transfer parameter value includes a first data transfer rate, and determining the transfer parameter value includes determining the first data transfer rate for a time point of a transfer of the first image dataset by predicting the first data transfer rate by applying a first trained function to a plurality of second data transfer rates.

9. A computer-implemented method for determining an imaging parameter value for control of a medical technology device during a capture of a first image dataset, wherein the first image dataset is to be transferred from the medical technology device to a remotely arranged device, the method comprising:

at least one of receiving or determining a transfer parameter value, wherein the transfer parameter value includes an information item concerning which image information is relevant for the first image dataset which is to be transferred;

determining the imaging parameter value based on the transfer parameter value; and providing the imaging parameter value, wherein the first image dataset comprises at least one medical image of an examination object, the transfer parameter value includes at least one of an information item concerning a movement of the examination object or an information item concerning a movement of an instrument situated within the examination object relative to the medical technology device, and the determining the transfer parameter value includes determining the information item concerning the movement of the examination object or the information item concerning the movement of the instrument by applying a trained function to at least one second image dataset.

10. The method of claim 9, wherein the imaging parameter value is determined such that a quality of the first image dataset is limited by the image information.

11. The method of claim 9, wherein the information item concerning the movement of the examination object or the information item concerning the movement of the instrument comprises at least one of an information item concerning a type of the movement or an information item concerning a velocity of the movement.

12. The method of claim 9, wherein the determining the information item concerning the movement of the examination object or the information item concerning the movement of the instrument includes:

determining an information item concerning a movement of the medical technology device for a time point of the capture of the first image dataset, wherein at least one of the information item concerning at least one of the movement of the examination object or the information item concerning the movement of the instrument depends upon the movement of the medical technology device.

13. The method of claim 9, wherein the determining the information item concerning the movement of the medical technology device is based upon at least one of at least one device parameter value of the medical technology device or a measurement value of at least one sensor arranged on the medical technology device.

14. The method of claim 9, wherein in the determining the information item concerning the movement of the medical technology device, the information item concerning the movement of the medical technology device is derived from an examination protocol.

15. The method of claim 9, wherein in the determining the information item concerning at least one of the movement of the examination object or the movement of the instrument, at least one of the information item concerning the-movement of the examination object or the information item concerning the movement of the instrument is determined by an edge analysis in the first image dataset.

16. The method of claim 9, wherein the imaging parameter value comprises at least one value for at least one of dose, image acquisition frequency, or binning.

17. The method of claim 9, further comprising:
transferring the first imaging dataset from the medical technology device to the remotely arranged device.

18. A non-transitory computer program product having a computer program which is directly loadable into a memory store of a determining system, the computer program having program portions that, when executed by the determining system, cause the determining system to perform the method of claim 9.

19. A non-transitory computer-readable storage medium having instructions, when executed by a determining system, configured to cause the determining system to perform the method of claim 9.

20. A determining system for determining an imaging parameter value for control of a medical technology device during a capture of a first image dataset, wherein the first image dataset is to be transferred from the medical technology device to a remotely arranged device, the determining system comprising:
an interface; and
a computing device, wherein
at least one of the interface or the computing device is configured to at least one of receive or determining a transfer parameter value,
the transfer parameter value comprises an information item concerning which image information is relevant for the first image dataset which is to be transferred,
the computing device is also configured to determine the imaging parameter value based on the transfer parameter value,
the interface is also configured to provide the imaging parameter value,
the first image dataset comprises at least one medical image of an examination object,
the transfer parameter value includes at least one of an information item concerning a movement of the examination object or an information item concerning a movement of an instrument situated within the examination object relative to the medical technology device, and
the determining the transfer parameter value includes determining the information item concerning the movement of the examination object or the information item concerning the movement of the instrument by applying a trained function to at least one second image dataset.

* * * * *